United States Patent
Malnekoff

(10) Patent No.: US 6,304,853 B1
(45) Date of Patent: Oct. 16, 2001

(54) AUTOMATED GEMSTONE EVALUATION SYSTEM

(76) Inventor: Peter J. Malnekoff, 5 S. Wabash, Suite 1010, Chicago, IL (US) 60603

( * ) Notice: Subject to any disclaimer, the term of this patent is extended or adjusted under 35 U.S.C. 154(b) by 0 days.

(21) Appl. No.: 09/157,470

(22) Filed: Sep. 21, 1998

(51) Int. Cl.⁷ .................................................. G06F 17/60
(52) U.S. Cl. .............................. 705/27; 705/400; 705/500
(58) Field of Search ............................... 705/27, 7, 8, 11, 705/10, 400, 500; 709/203, 219

(56) References Cited

U.S. PATENT DOCUMENTS

| | | |
|---|---|---|
| 3,660,649 | 5/1972 | Gilchrist et al. . |
| 3,752,966 | 8/1973 | Foy, Jr. et al. . |
| 3,944,368 | 3/1976 | Beesley . |
| 4,381,554 | 4/1983 | Reach et al. . |
| 4,394,580 | 7/1983 | Gielisse . |
| 4,782,448 | 11/1988 | Milstein . |
| 4,885,714 | 12/1989 | Eisenstein et al. . |
| 5,005,971 | 4/1991 | Davis . |
| 5,056,826 | 10/1991 | Suwa . |
| 5,064,281 | 11/1991 | Davis . |
| 5,143,212 | 9/1992 | Roberts et al. . |
| 5,317,503 | 5/1994 | Inoue . |
| 5,361,201 | 11/1994 | Jost et al. . |
| 5,383,129 | 1/1995 | Farrell . |
| 5,430,538 | 7/1995 | Kobayashi . |
| 5,615,005 * | 3/1997 | Valente et al. ..................... 356/30 |
| 5,758,144 * | 5/1998 | Eberhard et al. ................... 395/602 |
| 5,819,255 * | 10/1998 | Celis et al. ............................ 707/2 |
| 5,832,069 * | 11/1998 | Waters et al. ....................... 379/115 |
| 5,893,082 * | 4/1999 | McCormick ........................ 705/400 |
| 5,915,241 * | 6/1999 | Giannini .............................. 705/2 |
| 5,966,673 * | 10/1999 | Shannon ............................. 702/35 |
| 6,020,954 | 2/2000 | Aggarwal . |

FOREIGN PATENT DOCUMENTS 196 10 393
A1     9/1997  (DE) .

OTHER PUBLICATIONS

'Gemological Institute of America' Retrieved from the Internet: <URL: http://www.gia.org/>.*
'Diamonds and Diamond Grading European Gemological Laboratory' Retrieved from the Internet: <URL: http://www.egl.co.za/Default.htm>.*
'Washington Diamond', Retrieved from the Internet: <URL http://www.bigdiamond.com/>.*
Underwood, Thom, 'Windows software just for jewelers', Jewelers Circular Keystone, Oct. 1992, v163, n10, p108(2), Dialog File: 148: Gale Group Trade & Industry DB, Accession # 06207721.*
Engagement Diamond FAQ, Peter Mlynek, Aug. 1, 1995, <URL: www.wam.umd.edu/~sek/wedding/mlynek.html>.*
Diamond Price Estimator, <URL: www.usacerteddiamonds.com/diamondcalculator.html>.*

(List continued on next page.)

Primary Examiner—Tariq R. Hafiz
Assistant Examiner—Kyle J. Choi
(74) Attorney, Agent, or Firm—Rockey, Milnamow & Katz, Ltd.

(57) ABSTRACT

An automated gemstone evaluation system for producing a gemstone evaluation report and method for doing the same. The automated gemstone evaluation system receives gemstone data unique to the gemstone being evaluated from the user via an input device, like a keyboard for a computer. The automated gemstone evaluation system further includes a processor, which determines a pricing estimate and generates an evaluation report. The evaluation report is communicated to the user via an output device, and preferably includes a summary description of the qualities of the gemstone. The system and method further allow for the input to be received from a user located remotely and for the output to be returned to the remotely located user.

21 Claims, 3 Drawing Sheets

OTHER PUBLICATIONS

Diamond Helper: The Total Solution for Diamond Buyers, Inside Secrets for Diamond Buyers, <URL: http://diamondhunters.com/diamonds/products/vp.html>.*

Mervis Diamond Importers, e–diamonds.com, <URL: www.mervisdiamonds.com/inventory/diamonds/>.*

The Four C's, Tradeshop.com, <URL: www.tradeshop.com/master/four_c.shtml>.*

Engagement Ring Warehouse, <URL: www.midtnweb.com/engagement/index.shtml>.*

Diamond Price Calculator TM, Washington Diamond, <URL: www.bigdiamond.com/calculator.asp>.*

The Jewelry Judge (Product Description). Downloaded from Internet on Feb. 7, 2001 <URL: www.jewelryjudge.net>.*

"The Real Computer Payoff: Part 3" Jeweler's Cirulation–Keystone, v. CLXVI, n. 4, Apr. 1995, pp. 129+.*

Thompson, M. "Appraisal–Writing Software: More Than Just Pretty Reports" Jewelers Circular Keystone, v. 162, n. 2, Feb. 1991, pp. 226(7).*

"Gem/Jewelry Appraisals" 1996. Downloaded from Internet on Feb. 2, 2001 <URL: www.divorcesource.com/on/info/gems.html>.*

"Diamond Grading Information" 1996–2000. Downloaded from Internet on Feb. 8, 2001 <URL: www.awesomegems.com/diamondfacts.html>.*

"The 5C's" 1997–2001. Downloaded from Intenet on Feb. 2, 2001 <URL: www.diamondgrading.com/5Cs.htm>.*

Carat—Professional Jewelry Appraising Software (Product Description). Downloaded from Internet on Feb. 7, 2001 <URL: www.jewelryware.com>.*

Gemchecker (Product Description). Downloaded from Internet on Feb. 2, 2001 <URL: www.gemchecker.com>.*

Adamas Gemological Laboratory (Product Description). Downloaded from Internet on Feb. 7, 2001 <URL: www.gis-.net/~adamas/softeare.html>.*

Golding, M. "The Personal Computer: A Jeweler's Tool" Jewelers Circular Keystone, v. 162, n. 12, Dec. 1991, pp. 52(4).*

The Diamond Engagement Ring Buying Guide, <URL:http://diamondreview.com>.

Diamond Price Comparison and Buying Guide, <URL:http://www.pricescope.com>.

Olli Silven and Hannu Kauppinen, Recent Developments in Wood Inspection, International Journal of Pattern Recognition and Artificial Intelligence World Scientific, Feb. 1, 1996, pp. 83–95, vol. 10, No. 1, Singapore.

Richard Hartley, Alison Noble, James Grande & Jane Liu, Quantitative Measurement of Manufactured Diamond Shape, Computer Vision Third Conference on Computer Vision, May 2–6, 1994, pp. 433–440, ECCV 94, vol. 1, Stockholm.

Hard copy of internet page (http:/www.diamonds.net/about.htm).

Copy of Rapaport Diamond Report—partially redacted to remove confidential price data in the tables.

* cited by examiner

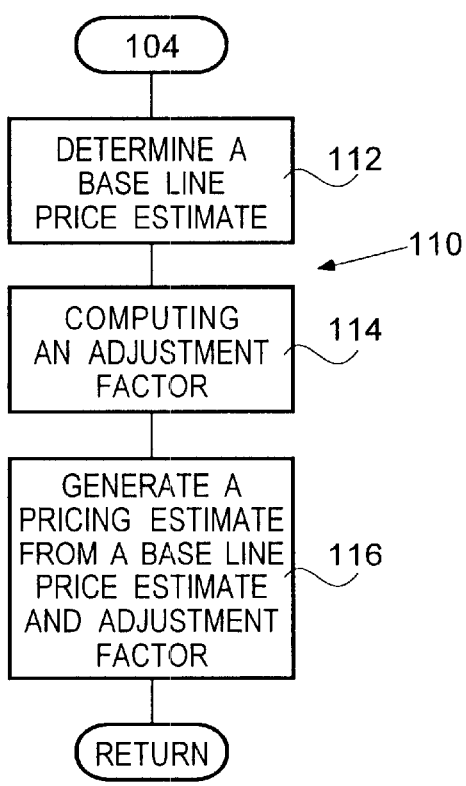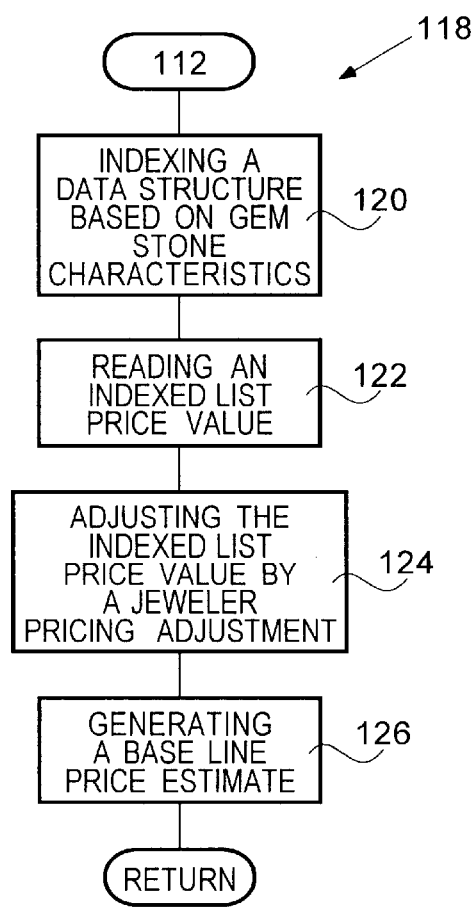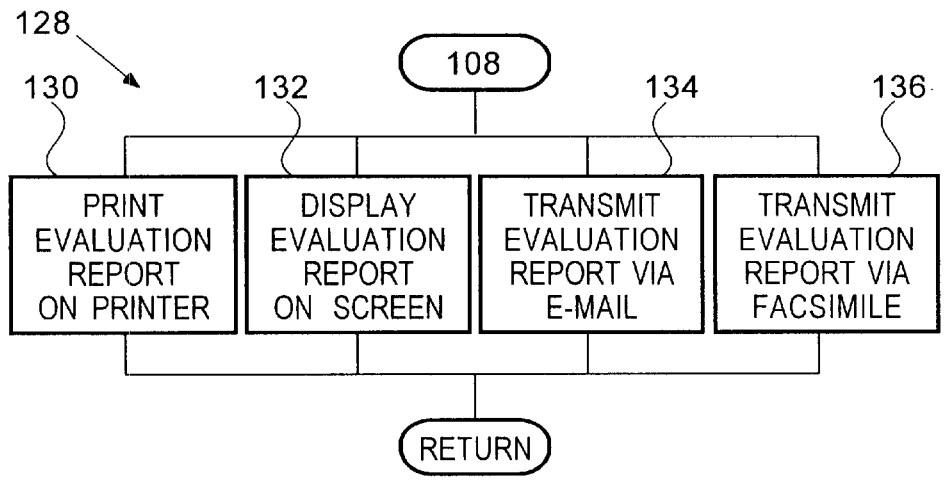

AUTOMATED GEMSTONE EVALUATION SYSTEM

BACKGROUND OF THE INVENTION

1. Field of the Invention

The present invention relates to an automated gemstone evaluation system and method for producing an automated gemstone evaluation report.

2. Description of the Related Art

As is the case for many unique or one of a kind items, individual gemstones, like houses, art, and used cars, can be difficult to determine the characteristics of quality to arrive at a fair market value. In many cases the only way to determine the fair market value of these types of items, is to determine what similar items have recently sold for. In addition to being able to identify similar items, which have been recently sold, one would also need to understand how the present item compares to the recently sold items, so as to be able to develop a reasonable approximation of the present item's fair market value. Analysis of this type typically requires a fair amount of experience and knowledge about a particular product's characteristics of quality and the market for that product.

However, for items like gemstones, many consumers do not buy and sell such items on a regular enough basis to develop the level of experience necessary to be able to approximate, with any degree of certainty, the values of the various gemstones they may see. Therefore they will often make an uninformed decision or will make use of an appraiser, who specializes in the valuation of items for a particular market.

For many of the gemstones being sold, the gemstone industry does provide a degree of objectivity to the gemstone buying process in the form of laboratory certificates. The laboratory certificates provide objective information specific to a particular gemstone, such as cut type, dimensions, weight, color and clarity. While the laboratory certificates help identify and rate various objective criteria, the typical consumer still does not have the requisite knowledge and experience to interpret the information, so as to evaluate the various gemstones. However a skilled appraiser can often times use the report to approximate a value for the gemstone without ever physically seeing the gemstone.

The appraiser further has available industry pricing reports, which provide close approximation pricing. The same industry pricing reports are often made reference to, by gemstone dealers, for a price reference point, during negotiations, when buying or selling gemstones with other gemstone dealers. However the industry pricing reports typically only provide a starting price point, and only take into consideration a subset of the objective criteria available from the various laboratory certificates. Furthermore, the objective criteria not taken into consideration by the industry pricing reports, unfortunately, often can and will have an impact on the fair market price, and need to be accounted for by the appraiser.

When shopping for a gemstone, like a diamond, it is not uncommon for a consumer to go to twenty or more jewelers and look at approximately five diamonds per jeweler. In a case such as this, the consumer can be comparing one hundred or more diamonds. If the consumer wants to determine the relative quality analysis and average buying price of all one hundred diamonds, the consumer would need to obtain one hundred evaluations.

Currently, for the typical consumer to obtain 100 evaluations, the consumer would obtain the services of a gemologist appraiser. The appraiser would manually review and analyze each gemstone, separately, and generate an evaluation for each gemstone for relative quality analysis and average buying price estimate. For a large number of gemstones this process of review can be very time consuming and expensive. Therefore it would be beneficial to develop an automated evaluation system, that is readily available to the general consumer, which takes into account additional objective data, which can affect the value of the gemstone, that the industry pricing reports do not take into account, and which the consumer does not understand how to correlate into the analysis process.

SUMMARY OF THE INVENTION

According to the present invention there is provided an automated gemstone evaluation system comprising an input device for receiving gemstone data, a processing device for generating an evaluation report including a pricing estimate, based upon the gemstone data received, and an output device for communicating the evaluation report to the user. Preferably the evaluation report includes a summary description of the gemstone.

The present invention further provides for a method for producing an automated gemstone evaluation report comprising the steps of receiving data describing a gemstone, computing a pricing estimate for the gemstone, based on data describing the gemstone received, generating an evaluation report including the pricing estimate, and communicating the evaluation report to the user.

One preferred aspect of the present invention provides for a remote access system, which allows gemstone data to be received from an input device located remotely, and the evaluation report to be communicated to a remotely located output device. The remote access system could make use of a private dial-up telephone connection, or could make use of a shared public network connection like the internet.

Other objects and advantages of the present application will be apparent from the detailed description and drawings which follow.

BRIEF DESCRIPTION OF THE DRAWINGS

FIG. 5 is a more specific flow diagram of the steps for computing a price estimate.

FIG. 6 is a more specific flow diagram of the steps for determining a baseline price estimate.

FIG. 7 is a more specific flow diagram of the steps for communicating an evaluation report to the user.

DESCRIPTION OF THE PREFERRED EMBODIMENT

Figure 1:
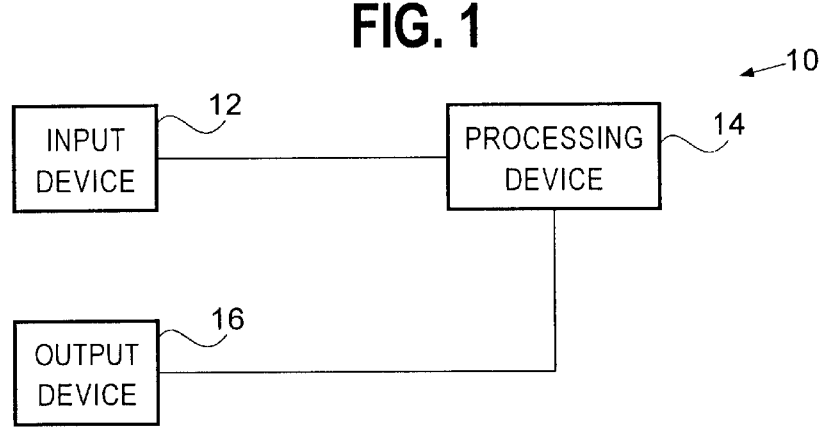
FIG. 1 is a block diagram of the major elements of an automated gemstone evaluation system, according to the teachings of the present invention.

Referring now to the drawings in greater detail, there is illustrated in FIG. 1 a block diagram of the elements of an automated gemstone evaluation system 10, according to the teachings of the present invention. The automated gemstone evaluation system 10 includes an input device 12 for receiving gemstone data. The input device 12 is coupled to a processing device 14, which receives the gemstone data from the input device 12. The processing device 14 generates an evaluation report including a pricing estimate, based upon the gemstone data received, and communicates the evaluation report to the user via an output device 16 coupled to the processing device 14.

Figure 2:
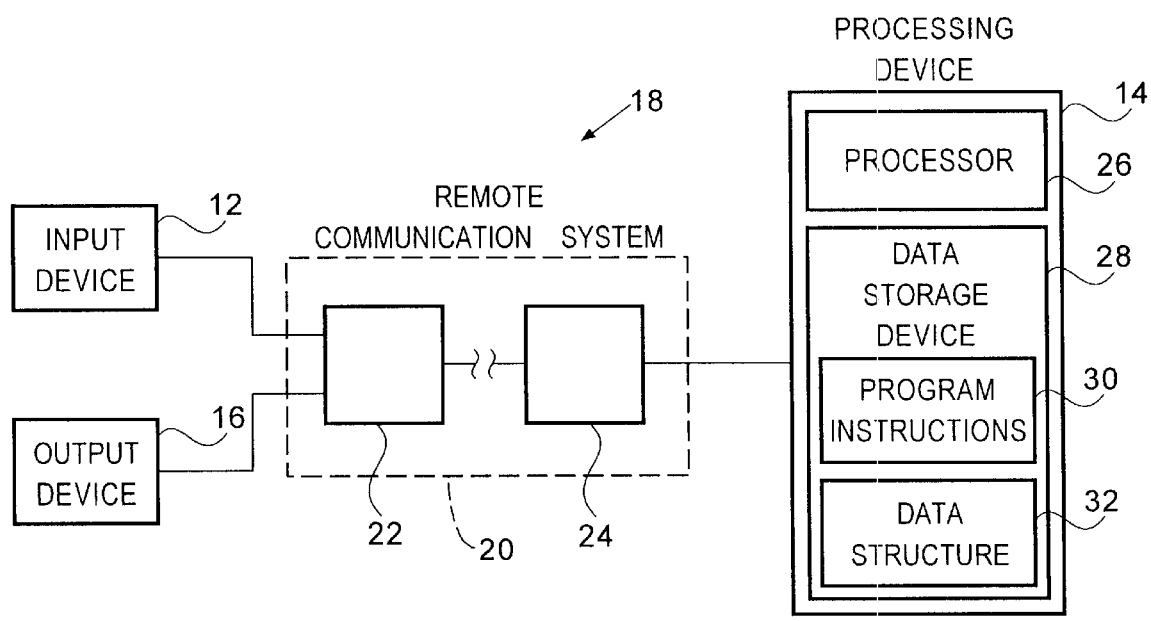
FIG. 2 is a more detailed block diagram of the automated gemstone evaluation system.

FIG. 2 is a more detailed block diagram 18 of the automated gemstone evaluation system, which additionally includes the preferred feature of a remote communication system 20. The remote communication system is coupled between the input device 12 and the processing device 14, and between the output device 16 and the processing device 14.

The remote communication system 20, allows the processing device 14 to remotely communicate with both the input device 12 and the output device 16. In the preferred embodiment the remote communication system 20 communicates over a shared public network, like the internet. In order for the devices to remotely communicate, the elements are connected to the remote communication system via communication access modules 22 and 24. The specific circuitry contained within the communication access modules 22 and 24 is dependent upon the method of communication used by the remote communication system 20 and the type of connection being made by the separate elements.

For example if communication is remotely established over a shared public network, like the internet, one possible configuration for the communication access module 24 coupled to the processing device 14 includes a network adapter card, which could subsequently be connected to hubs, transceivers, routers, and/or switches. Alternatively the connection could be provided by a dial-up modem connection through a network service provider.

Alternative to a connection over a shared public network is the possibility of a private connection through a direct dial connection, wherein both communication modules 22 and 24 could include dial-up modems connected to a POTS telephone connection. Another alternative could make use of radio transceivers, wherein communication could make use of a data signal transmitted and received over a radio frequency carrier signal. In fact the remote communication system 20 could make use of any of a number of different methods, which allow for remote communication.

Remote communication over a shared public network is preferable because it allows a single processing device 14 through a single connection to communicate to a large number of potential users.

However, in absence of a remote communication system 20, a processing device 14 could be attached locally to the input device 12 and the output device 16.

FIG. 2 further illustrates a more detailed block description of the processing device 14, which preferably includes a processor 26 and one or more data storage devices 28, like a memory for storing program instructions 30 and program data. At least some of the program data is preferably organized in the form of a database structure 32.

Figure 3:
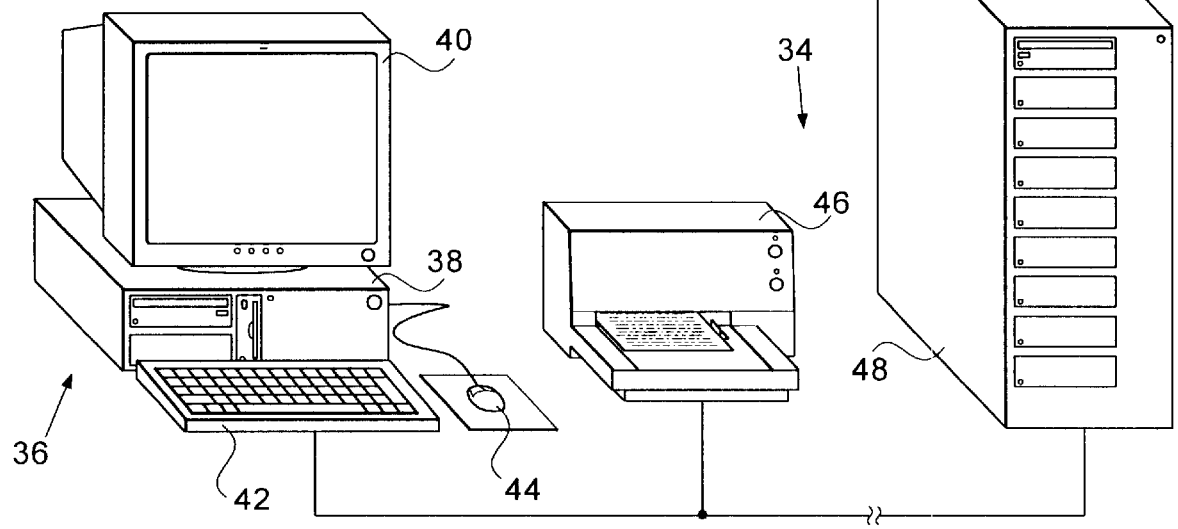
FIG. 3 is a perspective view of one example of system elements forming an automated gemstone evaluation system.

FIG. 3 illustrates a perspective view of a more specific example of system elements, which could be used for forming an automated gemstone evaluation system 34. The perspective view shows a computer 36, having a base unit 38 connected to a display screen 40, a keyboard 42 and a mouse 44. Shown proximate to the computer 36 is a second device 46, which is either a printer or a facsimile machine. Both the computer 38 and the second device 46 are shown connected to a server 48 or second computer.

In the example system the keyboard 42 and the mouse 44, in conjunction with the base unit 38, form the input device 12 through which a user can input gemstone information. The display screen 40 and the second device 46 form the output device 16, through which the user can receive a generated evaluation report. In the example shown, the processing device is embodied within the server 48, for the case wherein the processing device is located remotely. For the case wherein the processing device is located locally, the processing device could alternatively be embodied in the base unit 38 of the computer 36.

Figure 4:
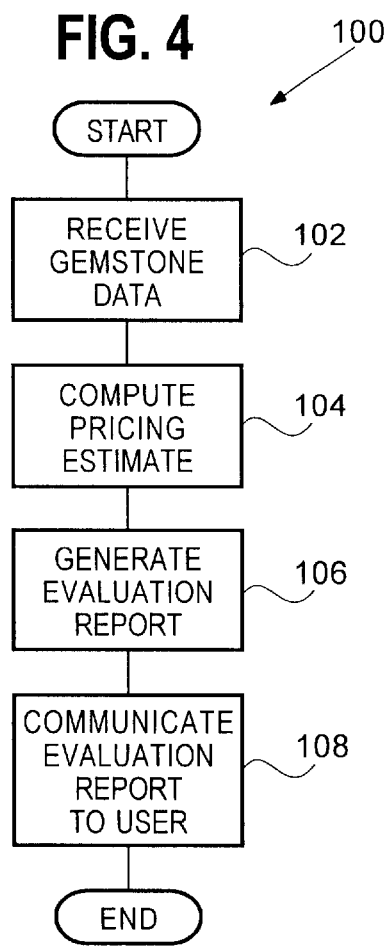
FIG. 4 is a flow diagram of the steps for producing an automated evaluation report.

While FIGS. 1–3 illustrate the block structure and examples of physical elements of the automated gemstone evaluation system, FIG. 4 illustrates a flow diagram of the method 100 for producing an automated evaluation report. The automated gemstone evaluation system produces an evaluation report by first receiving gemstone data 102 from the user via the input device 12. The gemstone data is then used by the processing device 14 to compute a pricing estimate 104. The processing device 14 further generates an evaluation report including the pricing estimate 106, and communicates the evaluation report to the user 108, via the output device 16.

In the preferred embodiment the gemstone data received 102, corresponds to the data contained on the various lab certificates typically associated with each gemstone. The gemstone data the system preferably uses includes cut type, weight (carats), color, clarity, cut proportions, fluorescence, and the identity of the lab generating the gemstone data. The information would preferably be typed using a keyboard 42 into the fields of an input screen displayed on the users computer 36, and sent to the processing device 14. Once the gemstone data has been received by the processing device 14, the processing device 14 computes a pricing estimate 104.

FIG. 5 illustrates a more specific flow diagram 110 of the preferred steps for computing a pricing estimate 104. In order to produce a pricing estimate the processing device 14 determines a baseline price estimate 112, utilizing some of the gemstone characteristics. The processing device 14 then computes an adjustment factor 114, based on other gemstone characteristics. The processor device 14 then uses the baseline price estimate and the adjustment factor to generate a pricing estimate 116.

FIG. 6 illustrates a more specific flow diagram 118 of the preferred steps for determining a baseline price estimate 112. The baseline price estimate is determined 112 by using some of the received gemstone characteristics, namely cut type, weight, color and clarity to index a data structure 120. A list price at the indexed location is then read from the data structure 122. The indexed list price is then adjusted by a variable jeweler pricing adjustment, dependent upon the current market conditions for the type of gemstone indexed 124. The indexed list price, adjusted by the appropriate jeweler pricing adjustment, is then used to generate the baseline price estimate 126.

As identified above in connection with FIG. 5, the baseline price estimate is then adjusted based on other gemstone characteristics, namely those characteristics not used in generating the baseline price estimate. Separate adjustments are computed based on cut proportions, fluorescence, and the identity of the lab generating the gemstone data.

Cut proportions can affect gemstone pricing, because the proportion will affect the look of the gemstone. In fact there can be as much as a 70 percent difference between the value of two diamonds having similar weight, color, clarity and cut type, as a result of differences in cut proportions. The cut proportions most appropriately used for further adjusting the price are depth percentage, table percentage, girdle thickness, crown height, crown angles, pavilion depth, pavilion angles, culet amount, and type of finish.

For example, depth percentage for a round cut diamond is determined by taking the total depth or height of the stone and dividing it by the average girdle diameter. A diamond having an ideal depth percentage will often positively affect the value of the diamond. An ideal depth percentage for a round cut diamond is around 58 percent.

As a further example, table percentage for a round cut diamond is determined by taking the widest table diameter and dividing it by the average width. Similar to depth percentage, a diamond having an ideal table percentage will likely have a positive affect on the value of the diamond. An ideal table percentage for a round cut diamond is around 56 percent.

As the value of the depth percentage or the table percentage of a gemstone varies from the ideal cut the amount of the adjustment will vary in a negative direction.

The automated gemstone estimation system has stored the appropriate amounts, that the various cut proportions will affect the value of the gemstone and adjusts the value accordingly.

Similarly the particular fluorescence of a gemstone, like a diamond, can positively and negatively affect the value of the gemstone. For example, a diamond having a blue fluorescence will often have a positive effect on the value, while a diamond having a yellow fluorescence will often have a negative effect. The amount of the effect can be dependent on other gemstone characteristics like color.

Another factor the automated gemstone evaluation system takes into account is the differences in grading by the different gemstone grading labs. Some labs grade more leniently, while other labs grade more harshly such that an equivalent rating for a particular gemstone characteristic determined by different labs will not necessarily be equivalent. Therefore the system needs to be able to make an adjustment based on the particular lab generating the laboratory certificate for the gemstone.

The automated gemstone evaluation system 10, when determining an adjustment factor 114, preferably takes into account all of these additional factors, and generates a final pricing estimate from the baseline price estimate and the adjustment factors 116.

The automated gemstone evaluation system 10, once it has a price estimate, generates an evaluation report 106. The evaluation report minimally includes the pricing estimate for the gemstone. However the evaluation report preferably additionally includes multiple price estimates for different types of retail outlets. For example a premium image retail store will likely charge more for a gemstone than a discount retail store. A negotiated discount price can be even lower. In the preferred embodiment the price estimates for the different types of retail outlets are determined by adjusting the original price estimate by a previously determined percentage.

Preferably the gemstone evaluation report will include a plain language descriptive entry for each of the characteristics, giving the consumer a general idea where the particular characteristic places the specific gemstone within the range of possible gemstones.

Once the gemstone evaluation system 10 generates the evaluation report 106, the system 10 will then communicate the report to the user 108. The system is preferably equipped to communicate the report in one of a plurality of ways. FIG. 7 illustrates a flow diagram 128 of the preferred steps for communicating an evaluation report to the user 108. The flow diagram 128 identifies at least four options. The evaluation report can be printed on a printer 130. The report can be displayed on the user's display screen 132. The report can be transmitted to the user via an electronic mail message 134. The report can be transmitted to the user via a facsimile message 136. Furthermore the user could request that the same evaluation report be communicated in multiple ways.

Wherein previous evaluations have been traditionally performed by human appraisers, which even if the appraiser can immediately perform the evaluation includes inherent delays in the time it takes to evaluate the characteristics of the gemstone and to compute a pricing estimate, in the present system the evaluation is performed in seconds by a processing device 14, like a computer. By automating the process and having a processing device perform the evaluation, the evaluation can be performed much more quickly, with the results being returned in a more timely and cost effective manner.

From the foregoing description, it will be apparent that the of the present invention has a number of advantages, some of which have been described above and others of which are inherent in the invention. Also it will be understood that modifications can be made to the automated gemstone evaluation system and method for producing an automated gemstone evaluation report described above without departing from the teachings of the invention.

I claim:

1. A consumer usable, fully automated gemstone evaluation system for which presence of the actual gemstone is not required, comprising:

an input device for receiving predetermined gemstone data values, supplied by a system user, of the type found on a gemstone laboratory grading certificate representing cut type, weight, color, clarity, and cut proportions, wherein the cut proportion data values represent at least two or more of depth percentage, table percentage, girdle thickness, crown height, crown angle, pavilion depth, pavilion angle, culet amount, and type of finish;

a processing device for computing a pricing estimate for use in a consumer evaluation report, wherein the processing device looks up an initial price value based at least in part upon the cut type, weight, color, and clarity data values supplied by the system user and automatically adjusts the initial price value based upon the two or more cut proportion data values in arriving at the pricing estimate; and an output device for communicating the evaluation report to the user.

2. The automated gemstone evaluation system according to claim 1, wherein said gemstone data values supplied by the system user include a value representing fluorescence, and wherein said processing device also adjusts the initial price value based upon the fluorescence value.

3. The automated gemstone evaluation system according to claim 1, wherein said evaluation report further includes a summary description of the qualities of the gemstone.

4. The automated gemstone evaluation system according to claim 1, wherein said pricing estimate is respective to different types of retail outlets.

5. The automated gemstone evaluation system according to claim 1, further comprising a remote communication section, allowing for the gemstone data to be received from an input device located remotely, and allowing for the evaluation report to be communicated to an output device located remotely.

6. The automated gemstone evaluation system according to claim 1, wherein said input device includes at least one of a keyboard and a mouse.

7. The automated gemstone evaluation system according to claim 1, wherein said processing device includes a processor and one or more data storage devices.

8. The automated gemstone evaluation system according to claim 7, wherein said one or more data storage devices includes a memory for storing program instructions and program data.

9. The automated gemstone evaluation system according to claim 8, wherein at least some of said program data is arranged in the form of a database structure.

10. The automated gemstone evaluation system according to claim 1, wherein said output device includes a printer for printing the evaluation report.

11. The automated gemstone evaluation system according to claim 1, wherein said output device includes a display screen for displaying the evaluation report.

12. The automated gemstone evaluation system according to claim 1, wherein said gemstone data values supplied by the system user include identity of a laboratory which generated the gemstone data, and wherein said processing device also adjusts the initial price value based upon said identity.

13. The automated gemstone evaluation system according to claim 1, wherein the system user is a consumer.

14. A fully automated method for producing a gemstone evaluation report, said method being consumer usable and without the presence of the actual gemstone being required, said method comprising the steps of:

receiving predetermined gemstone data values input by a user and of the type found on a gemstone laboratory grading certificate representing cut type, weight, color, clarity, and cut proportions, wherein the cut proportion data values represent at least two or more of depth percentage, table percentage, girdle thickness, crown height, crown angle, pavilion depth, pavilion angle, culet amount, and type of finish;

computing a pricing estimate for use in a consumer evaluation report, wherein this computing step includes looking up an initial price value based at least in part upon the cut type, weight, color, and clarity data values supplied by the user and automatically adjusting the initial price value based upon the two or more cut proportion data values in arriving at the pricing estimate; and communicating the evaluation report to the user.

15. The method of claim 14, wherein said step of receiving predetermined gemstone data values includes receiving a value representing fluorescence.

16. The method of claim 15, wherein said step of computing also adjusts the initial price value based on the fluorescence data value.

17. The method of claim 14, wherein said step of receiving gemstone data values includes receiving a value representing the identity of a laboratory which generated the gemstone data, and wherein said step of computing also adjusts the initial price value based upon said identity.

18. The method of claim 14, wherein said look-up step of determining the initial price value includes:

indexing a data structure, based upon the cut type, weight, color, and clarity of the gemstone; and reading an index price value stored in the data structure.

19. The method of claim 14, wherein said step of communicating the evaluation report to the user includes at least one of the steps of:

printing the evaluation report on a printer; and displaying the evaluation report on a display screen.

20. The method of claim 14, wherein said step of receiving gemstone data values includes receiving data values representing fluorescence and identity of a laboratory which generated the gemstone data, and wherein said step of computing also adjusts the initial price value based upon said fluorescence and identity data values.

21. The method of claim 14, wherein the user is a consumer.

* * * * *